(12) United States Patent
Lamoncha

(10) Patent No.: US 9,659,269 B2
(45) Date of Patent: May 23, 2017

(54) SYSTEM AND METHOD FOR INCREASING EMPLOYEE PRODUCTIVITY

(76) Inventor: Mark Lamoncha, Columbiana, OH (US)

( * ) Notice: Subject to any disclaimer, the term of this patent is extended or adjusted under 35 U.S.C. 154(b) by 470 days.

(21) Appl. No.: 12/748,895

(22) Filed: Mar. 29, 2010

(65) Prior Publication Data
US 2010/0250343 A1   Sep. 30, 2010

Related U.S. Application Data

(60) Provisional application No. 61/164,220, filed on Mar. 27, 2009.

(51) Int. Cl.
*G06Q 10/06* (2012.01)
*C12Q 1/68* (2006.01)

(52) U.S. Cl.
CPC ... *G06Q 10/06398* (2013.01); *G06Q 10/0639* (2013.01); *C12Q 1/6883* (2013.01); *C12Q 2600/156* (2013.01); *G06Q 10/063114* (2013.01)

(58) Field of Classification Search
CPC ......... G06Q 10/0639; G06Q 10/06398; G06Q 10/063114; C12Q 2600/118; C12Q 2600/156
See application file for complete search history.

(56) References Cited

U.S. PATENT DOCUMENTS

| | | | |
|---|---|---|---|
| 3,035,355 A * | 5/1962 | Holmes | 434/238 |
| 3,967,261 A * | 6/1976 | Fudaley | 173/2 |
| 4,408,204 A | 10/1983 | Salvesen | |
| 4,615,197 A * | 10/1986 | Allebach | 72/88 |
| 4,800,502 A | 1/1989 | Stewart et al. | |
| 5,134,574 A | 7/1992 | Beaverstock et al. | |
| 5,429,373 A * | 7/1995 | Chelko et al. | 273/440 |
| 5,459,657 A | 10/1995 | Wynn | |
| 5,717,867 A | 2/1998 | Wynn | |
| 5,754,965 A * | 5/1998 | Hagenbuch | 701/32.5 |
| 5,842,182 A | 11/1998 | Bonner | |
| 6,034,970 A * | 3/2000 | Levac et al. | 370/466 |
| 6,119,097 A | 9/2000 | Ibarra | |
| 6,125,356 A * | 9/2000 | Brockman et al. | 705/37 |
| 6,160,528 A | 12/2000 | Carpine et al. | |

(Continued)

OTHER PUBLICATIONS

Lazear, Edward, 2000, Performance Pay and Productivity, The American Economic Review, vol. 90, No. 5, pp. 1346-1361.*

(Continued)

*Primary Examiner* — Matthew Gart
*Assistant Examiner* — Stephen S Swartz
(74) *Attorney, Agent, or Firm* — Standley Law Group LLP

(57) ABSTRACT

An exemplary embodiment of the computerized system and method for increasing employee productivity provides a database for storing data, a data inputting device for inputting expected output parameters into the database and a data acquiring device for acquiring actual output data during performance of any workplace duties, preferably in real-time. The data acquiring device may be linked by an interface that transfers the acquired data to the database, where a processor may evaluate the inputted data versus the acquired data. The processor is connected to a data displaying device that may display the inputted, acquired and evaluated data, preferably in real-time.

6 Claims, 3 Drawing Sheets

(56) References Cited

U.S. PATENT DOCUMENTS

| | | | |
|---|---|---|---|
| 6,336,053 B1* | 1/2002 | Beatty | 700/108 |
| 6,347,306 B1* | 2/2002 | Swart | 705/32 |
| 6,356,875 B1* | 3/2002 | Green et al. | 705/7.37 |
| 6,507,765 B1* | 1/2003 | Hopkins | G05B 19/41875 29/705 |
| 6,681,197 B2 | 1/2004 | Brunner et al. | |
| 6,815,650 B1* | 11/2004 | Bartz | 219/663 |
| 7,114,648 B2 | 10/2006 | Ginskey | |
| 7,197,638 B1* | 3/2007 | Grawrock et al. | 713/165 |
| 7,228,192 B2* | 6/2007 | Popplewell | 700/115 |
| 7,249,051 B1 | 7/2007 | Jenniges et al. | |
| 8,015,454 B1* | 9/2011 | Harrison et al. | 714/47.3 |
| 8,040,292 B2* | 10/2011 | Ronzani et al. | 345/8 |
| 8,209,243 B2 | 6/2012 | Smith | |
| 2002/0091498 A1* | 7/2002 | Brunner | G05B 19/41875 702/182 |
| 2002/0103569 A1 | 8/2002 | Mazur | |
| 2002/0143423 A1 | 10/2002 | Huber et al. | |
| 2002/0165749 A1 | 11/2002 | Northcutt | |
| 2003/0014498 A1* | 1/2003 | Kreidler | G05B 19/0426 709/217 |
| 2003/0233163 A1* | 12/2003 | Dorsch | 700/117 |
| 2004/0044733 A1 | 3/2004 | Fan | |
| 2004/0148136 A1* | 7/2004 | Sasaki | G05B 19/4065 702/188 |
| 2005/0130633 A1* | 6/2005 | Hill et al. | 455/414.1 |
| 2005/0137735 A1* | 6/2005 | Loy et al. | 700/109 |
| 2005/0165585 A1* | 7/2005 | Bhateja | B24B 51/00 702/188 |
| 2006/0010051 A1 | 1/2006 | Sattler | |
| 2006/0020509 A1 | 1/2006 | Strain et al. | |
| 2006/0259160 A1 | 11/2006 | Hood et al. | |
| 2009/0192926 A1 | 7/2009 | Tarapata | |
| 2009/0204234 A1* | 8/2009 | Sustaeta et al. | 700/29 |
| 2010/0153263 A1* | 6/2010 | Keadle et al. | 705/39 |

OTHER PUBLICATIONS

Ludwig Tom, Goomas David, 2007, Enhancing Programs with Proximal Goals and Immediate Feedback: Engineered Labor Standards and Technology Enhancements in Stocker Replenishment, Journal of Organizational Behavior Management.*

* cited by examiner

SYSTEM AND METHOD FOR INCREASING EMPLOYEE PRODUCTIVITY

CROSS REFERENCE TO RELATED APPLICATIONS

This application is a non-provisional application of U.S. 61/164,220 filed Mar. 27, 2009 which is hereby incorporated by reference as if fully recited herein

INVENTIVE FIELD

Exemplary embodiments of the present invention are directed to a system and method for increasing employee productivity. More particularly, exemplary embodiments of the present invention are directed to a system and method for increasing employee productivity by illustrating the employee's pay rate directly to the employee.

BACKGROUND OF THE INVENTIVE FIELD

In any workplace setting the production of each individual is vital for overall success of the company. In any workplace setting, the main way to increase the profitability of the company is to measure and increase the productivity of each and every employee. There have been numerous studies and a countless amount of research to find ways to increase employee productivity. The result of this research indicates that a vital way to increase productivity of employees is to provide each and every employee with incentive to safely increase both the quantity and quality of their output. This may be accomplished by giving each employee personal responsibility within the process for the amount and quality of work they perform.

Oftentimes, in the workplace setting, the personal responsibility of employees consists mainly of meeting certain standards, expectations or goals during their scheduled work time. Furthermore, employees typically get paid by an hourly or salary rate. Consequently, employees have no real incentive to perform at any levels higher than the minimum goal number; as they will be paid the same amount of money regardless of any excess amount of output over the minimum goal. Accordingly, the employees see a disconnect between the employees realizing their individual increase in output and the employees being rightfully compensated for improvements in safety, quality and productivity Normally, employers provide incentives to employees by providing compensation through increases in hourly rates, salary or periodic bonuses. However, many employees do not consider these as adequate forms of compensation. It may take weeks, months or even years before employees recognize the fruits of his or her individual labor. Furthermore, on a weekly or even shift basis, most employees do not have a way to evaluate if or how they may be adequately compensated if they go above the call of duty and perform above the minimum goals. Most employees do not have trust in management that they will be adequately compensated.

Consequently, it can be understood that there is a need for a system and method for increasing employee productivity. Preferably, such a system and method would provide employees with real-time incentive to safely increase the amount and quality of their individual output. It would also be preferable that such a system and method would make each employee individually accountable for the amount of compensation they earn. Preferably, such a system and method may also provide timely monetary compensation for employees. Additionally, it is preferred that the system and method may have integrated safety and quality systems. A system and method of an exemplary embodiment of the system and method for increasing employee output may satisfy all or some of these needs/preferences.

SUMMARY OF THE GENERAL INVENTIVE CONCEPT

One example of the present invention is directed to a system and method for igniting the spirit of human competition within the worker by encouraging them to safely increase productivity translating to their increased monetary compensation and their reward of meeting and beating production goals without sacrificing quality. More particularly, one example of the present invention is directed to a system and method for increasing employee compensation by illustrating the employee's pay rate in "real time" directly to a system that displays on any electronic device, stationary or portable, such as on a pay rate watch.

Generally speaking, an exemplary embodiment of the computerized system and method for increasing employee productivity provides a database for storing data, a data inputting device for inputting expected output parameters into the database and a data acquiring device for acquiring actual output data during performance of any workplace duties, preferably in real-time. The data acquiring device may be linked by an interface that transfers the acquired data to the database, where a processor may evaluate the inputted data versus the acquired data. The processor is connected to a data displaying device that may display the inputted, acquired and evaluated data, preferably in real-time.

Preferably, the system and method includes a data correcting device for correcting the actual production data after the production data has been acquired. It may be preferred that an exemplary embodiment includes a network that links to a machine's PC to the machine's PLC. In some exemplary embodiments, the machine's PLC may be controlled by and interrupted by the machine's PC for safety and quality related training and/or warnings in the form of e-mails and training presentation software. In some embodiments, the machine's PC allows a user to correct actual production data and shut down the machine. It is also preferred that an embodiment may include any portable or stationary data displaying device or any pay rate watch device adapted to secure around a user's wrist and is adapted to link with the processor. In another embodiment, the system and method includes a safety and quality control system that is adapted to lockout the machine whenever the employee identification number is not on an approved list of employee identification numbers stored in the database. In another embodiment, the system and method may link with a banking system for distributing a daily payroll or direct deposit of an employee's earned wages.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
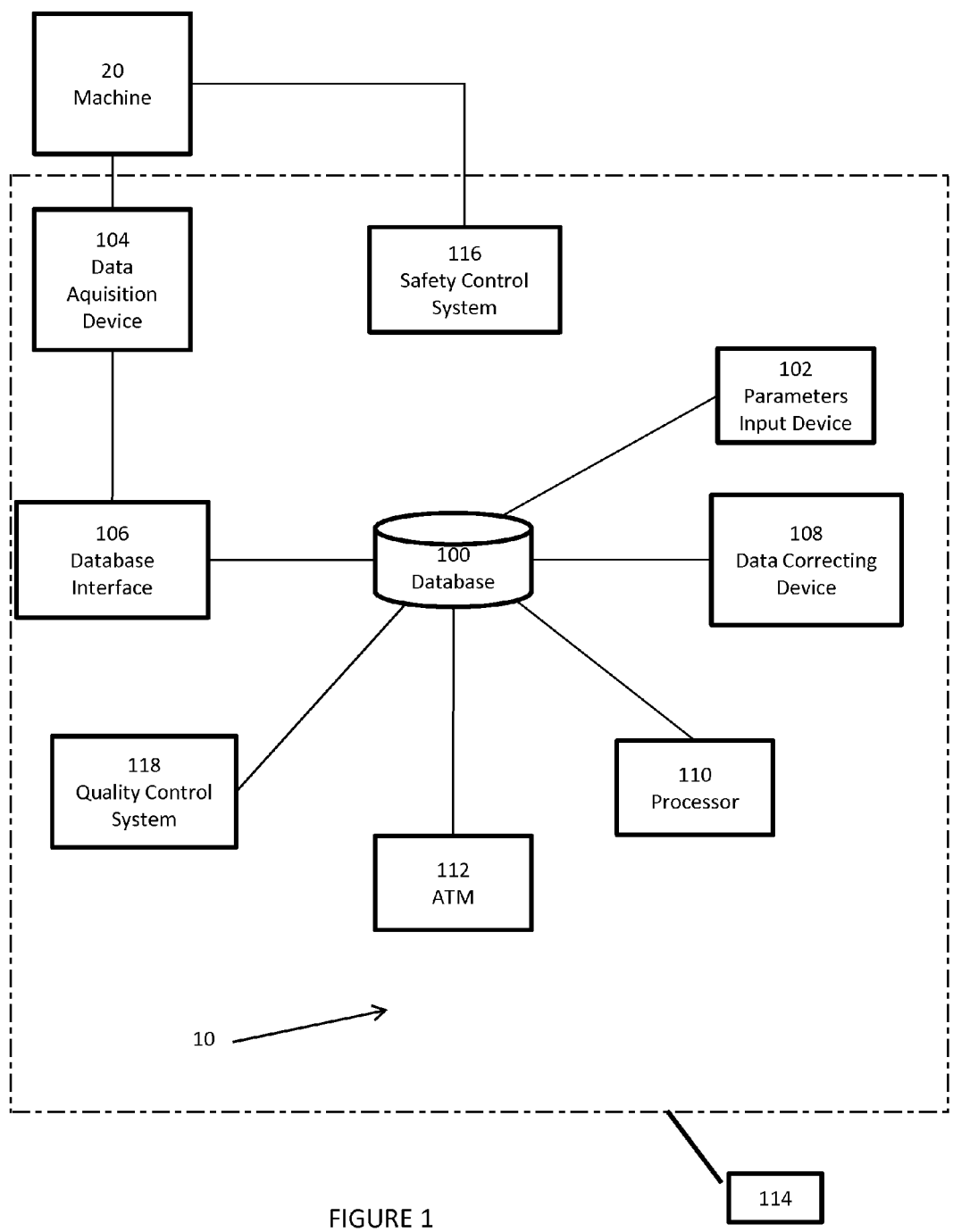
FIG. 1 is a schematic view illustrating one exemplary embodiment of a system for increasing employee productivity in a production process on a machine.
Figure 2:
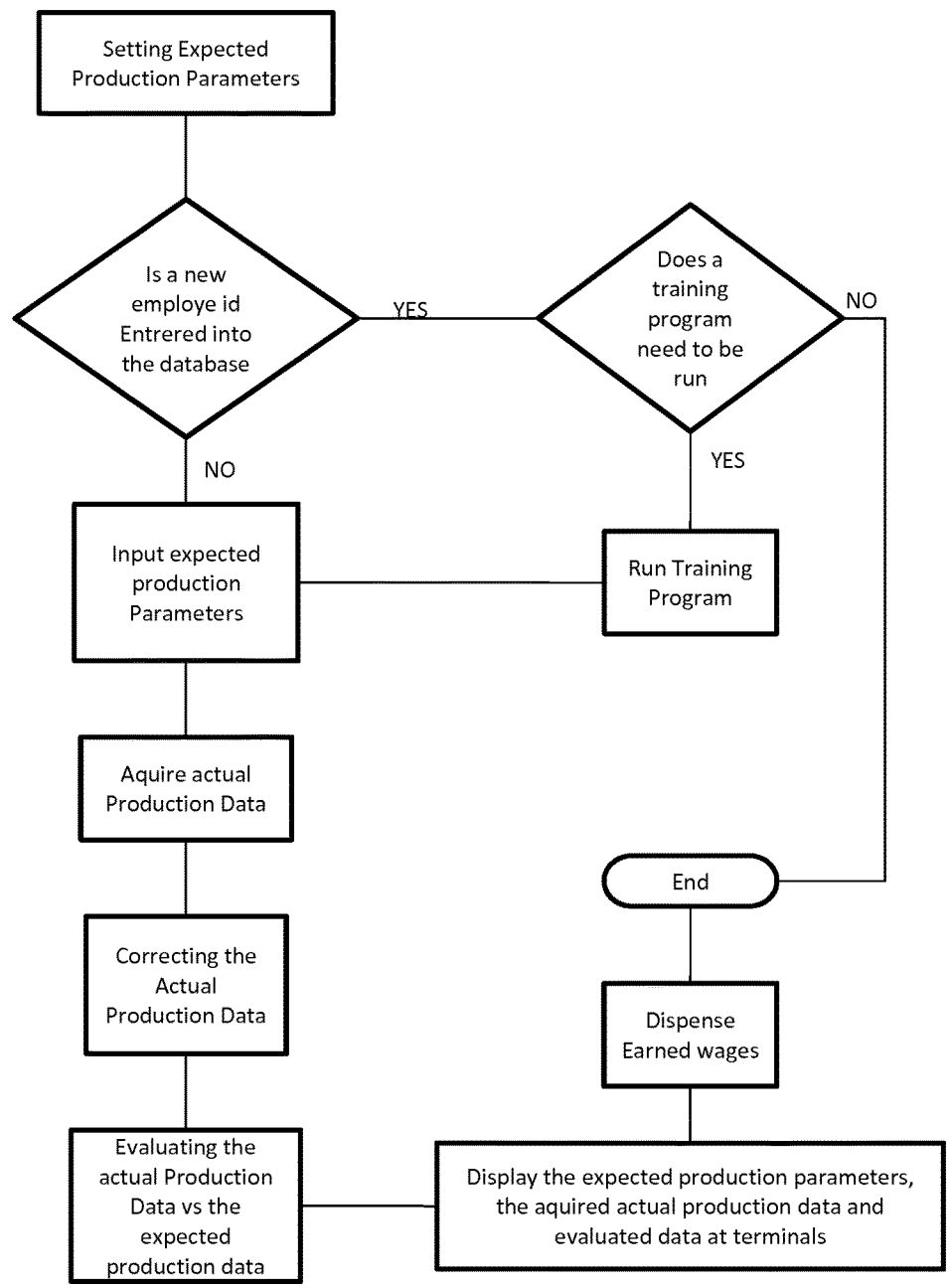
FIG. 2 is flow diagram illustrating the steps of an exemplary embodiment of the method for increasing employee productivity in a production process on a machine.

FIG. 1 depicts a schematic of one exemplary embodiment of a system 10 for increasing employee productivity in a production process on a machine (hereinafter "system"). Similarly, FIG. 2 is flow diagram illustrating the steps of an exemplary embodiment of the method for increasing employee productivity in a production process on a machine. As shown, this particular system 10 is shown to have a database 100 for storing data, a data inputting device for inputting expected production parameters 102 into the database 100, a data acquiring device for acquiring actual production data 104 from the machine 20, an interface 106 for transferring the acquired production data to the database 100, and a data correcting device for correcting actual production data 108 after the production data is acquired. Additionally, this embodiment of the system 10 includes a processor 110 for evaluating the inputted data versus the acquired data, a data displaying device 112 for displaying the inputted, acquired and evaluated data, a computer network 114 that links the machine to the database 100, and the data displaying device 112, a safety control system 116, a quality control system 118, and an automated telling machine 120.

In this embodiment, a data inputting device for inputting expected production parameters 102 into the database 100 for storing data is a computer terminal that is in connection with the database 100. Typically, production parameters that may be inputted in the database 100 include, but are not limited to: standard time to fabricate an individual part; standard rate of pay per part; standard pay rate per minute, hour, shift, week, month, year; standard number of parts fabricated in an minute, hour, shift, week, month, year; employee's name; employee's identification from fingerprints, retinal scan, DNA, etc.

The system 10 includes a data acquiring device for acquiring actual production data 104 from a machine, which in this particular embodiment, is a programmable logic controller that is linked to multiple sensors. Typically, actual production data acquired may include, but is not limited to: total parts produced per second, minute, hour, shift, week, month, year; scrap rate per second, minute, hour shift, week, month, year; total machine run time; runtime per part, shift, week, month, year; total machine downtime; downtime per part, shift, week, month, year; product quality data; machine safety data, etc. Typically, but not necessarily, the actual production data may be acquired automatically and in real-time.

Furthermore, in this particular embodiment, an interface 106 transfers the acquired production data to the database 100. The interface 106 may be any type of connection that includes, but is not limited to: cable or telephone lines, the Internet, satellite links, etc. In this particular embodiment, the interface 106 is wired. However, in other exemplary embodiments, the interface 106 may be wireless.

Although it is preferred that an embodiment of the system 10 includes a data correcting device for correcting actual production data 108 after the production data is acquired, it is not required. In this embodiment, the data correcting device 108 is a computer terminal that is in connection with the database 100. Preferably, but not necessarily, the computer terminal is the same computer terminal used to input production parameters. In other embodiments, the data correcting device 108 may be a keypad or keyboard linked with a programmable logic controller.

This particular embodiment includes a processor 110 for evaluating the inputted production parameters versus the acquired production data to produce evaluated data. The processor 110 executes algorithms to produce the evaluated data. The following are a couple of examples of algorithms that may be performed by the processor 110 given the inputted production parameters and the acquired data. These examples are in no way limiting the capability of the numerous different algorithms the processor 110 may execute. One simple example of a typical algorithm executed by the processor may produce the total realized pay for an employee for a shift that could be set forth in a relationship such as, but not limited to:

$TRPS = X * TPPS$ where:

TRPS is the total realized pay for an employee for a shift;
X is the standard pay rate per part; and
TPPS is the total parts produced for a shift.

In this example, the standard pay rate per part would be inputted into the database 100 as one of the performance parameters and the total parts produced for a shift would be actual data acquired from the machine during the production process. In another example, the algorithm may produce the difference between expected pay per shift and the realized pay per shift that could be set forth in a relationship such as, but not limited to:

$DEPRP = X * TPPS - EPS$ where:

DEPRP is the difference between the expected pay and realized pay per shift
X is the standard pay rate per part;
TPPS is the total parts produced for a shift; and
EPS is the expected pay per shift.

In this example, the standard pay rate per part and the expected pay per shift would be inputted into the database 100 as one of the performance parameters and the total parts produced for a shift would be actual data acquired from the machine during the production process.

In another example, the algorithm may produce the realized hourly rate by an employee that could be set forth in a relationship such as, but not limited to:

$RHR = [TPPS/T] * X$ where:

RHR is the realized hourly rate
TPPS is the total parts produced for a shift;
T is total time in hours; and
X is the standard pay rate per part.

In this example, the standard pay rate per part would be inputted into the database 100 as one of the performance parameters and the total parts produced for a shift and the total time in hours would be actual data acquired from the machine during the production process.

Normally, the processor 110 may produce evaluated data including, but is not limited to: difference between expected pay and realized pay per second, minute, hour, shift, week, month, year; realized pay per minute, hour, shift, week, month year; realized pay-rate per hour, shift, week, month, year; difference between expected and realized parts produced per minute, hour, shift, week, month, year; quality data, and safety data. Typically, but necessarily, the evaluated data is produced automatically and in real-time.

Figure 3:
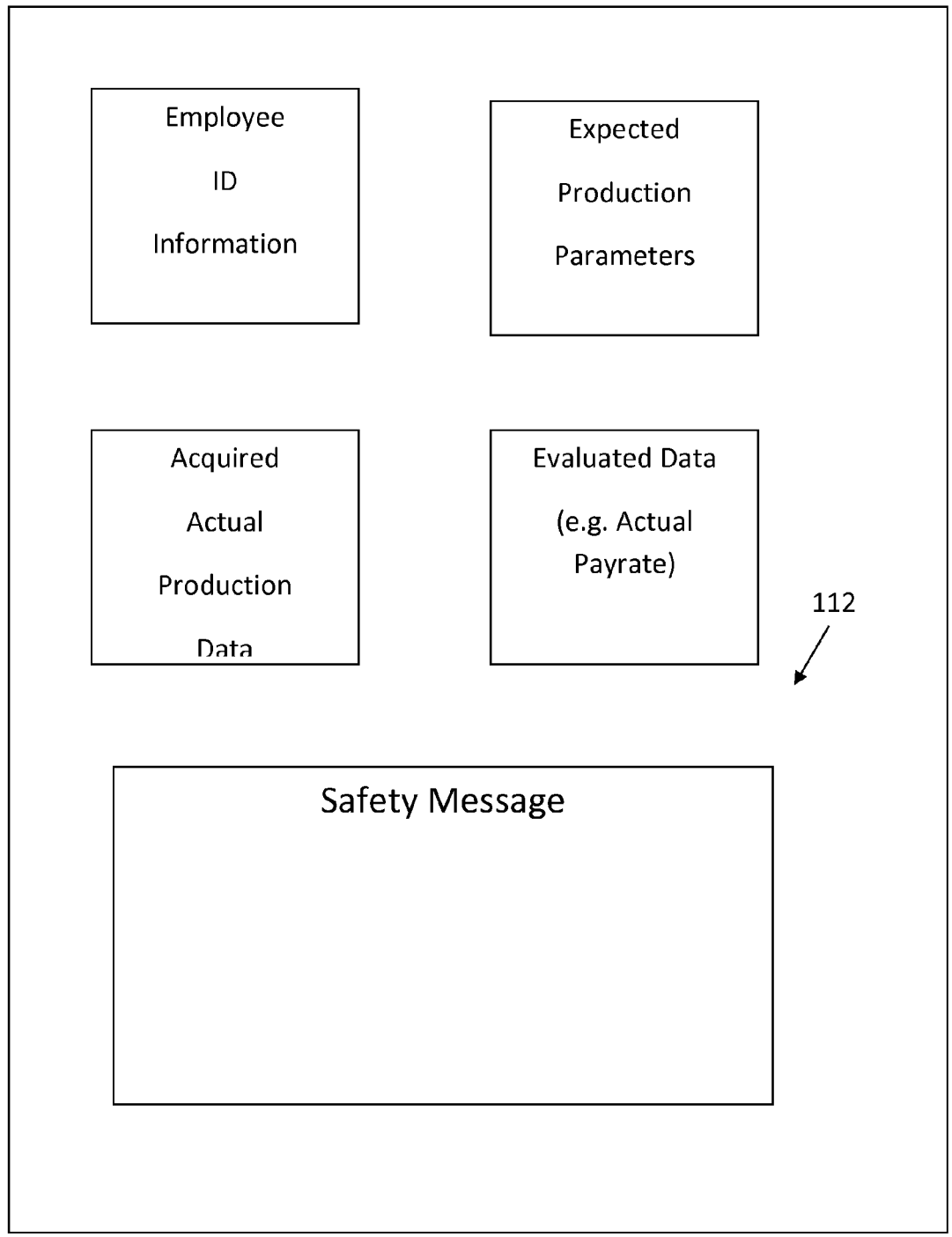
FIG. 3 is a screenshot illustrating an exemplary embodiment of the means for displaying data.

In one particular embodiment, the system 10 includes a data displaying device 112 that may display the inputted, acquired and evaluated data that is adapted to connect to the database 100. An example of a screenshot of an exemplary embodiment of the data displaying device is illustrated in FIG. 3. In this particular embodiment, the means for displaying 112 is an electronic display. Preferably, but not necessarily, the data displaying device 112 is located within visible sight of the employee operating a machine to help provide incentive to the employee to increase both production rate and quality. In this regard, the data displaying device 112 may be a portable device that is adapted to connect to the database 100 using a wireless network. Preferably, but not necessarily, the portable display device may be adapted to secure around an individual's wrist, the result being a device that may resemble a wristwatch. In another other embodiment, the portable device may be adapted to secure to an individual's belt. However, in other embodiments, the data displaying device 112 may be any type of display screen that may be adapted to connect to the database 100 through a wireless or wired connection. In one exemplary embodiment, the data displaying device 112 may be a monitor for a computer. In some exemplary embodiments, the data displaying device 112 is engaged with and adjacent to a machine on an assembly line or in the employee's workstation to ignite the spirit of human competition within the worker by encouraging them to safely increase productivity translating to their increased monetary compensation and their reward of meeting and beating production goals without sacrificing quality.

In whatever form, all the components of the system 10 are preferably linked by a network 114. However, the network 114 may link any and/or all components of the system 10. One skilled in the art would realize that there are many different ways to network the components, including, but not limited to: cable or telephone lines, the Internet, satellite links. In this particular embodiment, the network is wireless. However, in other exemplary embodiments, the network 114 may be wired and/or wireless, depending upon the design factors and other considerations, as would understood by one skilled in the art.

In this particular embodiment, the system 10 includes a safety control system 116 adapted to communicate with the machine. Although the safety control system 116 is preferred, other exemplary embodiments of the system 10 may not include such a safety control system 116. In one particular embodiment, the safety control system 116 may have a terminal wherein an individual may input an individual identification code. In this embodiment, depending upon the identification code entered, the machine may lockout whenever the employee identification number is not on a secured list in the database.

In other exemplary embodiments, the safety and quality control system 116 may control a machine's PLC and interrupt operation of the machine. In this particular embodiment, the safety control system 116 is controlled by a PC. In some embodiments, the safety control system 116 may interrupt the machine's PC for safety or quality related training and/or warnings in the form of emails and training presentation software. In one example, at the start of a shift, the safety control system 116 may walk a worker through a training exercise before the worker may start working. In another example, an administrator or another authorized individual may send the machine's PC an email message that must be read by a worker before the machine will start or continue operating.

In order to provide timely incentive rewards for employees, a banking system 118 for distributing a daily payroll or direct deposit of an employee's earned wages may be linked with the system 10 to provide an amount of money earned by the employee. In this particular embodiment, an individual may obtain the amount of money they earned from an automated telling machine at the end of each production shift. However, in other embodiments, the banking system 118 may allow the employee to obtain the amount of money they earned at varying time intervals, such as, but not limited to: each hour, daily, weekly, monthly, yearly or each break period. In yet another embodiment, the banking system 118 may provide other forms of compensation by itself, or in addition to monetary compensation. One example may be where the banking system 118 may provide employees with tokens that the employee may spend at a company store. In other embodiments, the banking system 118 may directly deposit the employee's earned wages into a predetermined banking or checking account.

While certain embodiments of the present invention are described in detail above, the scope of the invention is not to be considered limited by such disclosure, and modifications are possible without departing from the spirit of the invention as evidenced by the following claims:

What is claimed is:

1. A system for increasing employee productivity in a production process, comprising:
    a database for storing employee production parameters including a pay rate per part produced in a production process (X);
    a PLC linked to a sensor for acquiring from a machine during a production process actual employee production data in real-time including the number of parts produced (TPPS);
    an interface for transferring the actual employee production data to a processor that executes instructions to:
    (a) Calculate the amount of time (T) spent to produce the number of parts TPPS; and
    (b) produce real-time employee production pay data by calculating (TPPS/T) * X: and
    a data displaying device, mounted on or near the machine, for displaying at least the real-time employee production pay data to an employee while engaged in the production process so as to increase the real-time productivity of the employee.

2. The system of claim 1, further comprising a network that links the database with the data displaying device
    wherein the network is adapted to communicate at least the real-time employee pay data to the data displaying device.

3. The system of claim 1, wherein the data displaying device is portable device adapted to link with the data thru a wireless network, and is adapted to secure around an individual's wrist.

4. The system of claim 1, further comprising a safety control system adapted to lockout the machine whenever the employee identification number is not on a secured list in the database.

5. The system of claim 1, further comprising a safety control system that is adapted to interrupt operation of the machine for safety or quality related training or warnings.

6. The system of claim 1, further comprising a banking system that is adapted to dispense an amount of money earned by the employee.

* * * * *

UNITED STATES PATENT AND TRADEMARK OFFICE
CERTIFICATE OF CORRECTION

| | | |
|---|---|---|
| PATENT NO. | : 9,659,269 B2 | Page 1 of 1 |
| APPLICATION NO. | : 12/748895 | |
| DATED | : May 23, 2017 | |
| INVENTOR(S) | : Mark Lamoncha | |

It is certified that error appears in the above-identified patent and that said Letters Patent is hereby corrected as shown below:

In the Title:
Please delete "AND METHOD".
In Claim 3:
Column (6) Line 53, please insert --a-- in between "is" and "portable".

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*